United States Patent
Namespetra et al.

(10) Patent No.: US 7,959,872 B2
(45) Date of Patent: Jun. 14, 2011

(54) SYSTEM AND DEVICE FOR WATER FILTRATION AND PURIFICATION

(75) Inventors: Justin L. Namespetra, Essex (CA);
Scott P. Hickey, Niagara Falls (CA);
Steve L. Hengsperger, Lakeshore (CA)

(73) Assignee: Tersano Inc., Oldcastle, Ontario (CA)

( * ) Notice: Subject to any disclaimer, the term of this patent is extended or adjusted under 35 U.S.C. 154(b) by 0 days.

(21) Appl. No.: 12/730,635

(22) Filed: Mar. 24, 2010

(65) Prior Publication Data

US 2010/0176037 A1    Jul. 15, 2010

Related U.S. Application Data

(62) Division of application No. 10/562,206, filed as application No. PCT/CA2004/000946 on Jun. 25, 2004, now Pat. No. 7,708,958.

(60) Provisional application No. 60/482,519, filed on Jun. 26, 2003.

(30) Foreign Application Priority Data

Jan. 9, 2004   (WO) ............... PCT/CA2004/000043
Jan. 12, 2004  (WO) ............... PCT/CA2004/000042

(51) Int. Cl.
*C02F 1/78* (2006.01)

(52) U.S. Cl. .................. 422/300; 210/748.08; 210/192; 210/266; 210/760

(58) Field of Classification Search ............. 210/748.01, 210/739, 600, 167, 760; 422/300, 292, 20
See application file for complete search history.

(56) References Cited

U.S. PATENT DOCUMENTS

| 3,024,138 A | 3/1962 | Scholott |
| 3,426,513 A | 2/1969 | Bauer |
| 3,775,314 A | 11/1973 | Beitzel et al. |
| 3,904,362 A | 9/1975 | DiPaolo |

(Continued)

FOREIGN PATENT DOCUMENTS

CA    2296129    4/2001

(Continued)

OTHER PUBLICATIONS

U.S. Appl. No. 60/431,125 Author: Vandenbelt, Rudy, Application Title: Water Filter, Effective Filing Date: Dec. 5, 2002, Pertinent Pages: Whole Document.*

(Continued)

*Primary Examiner* — Walter D Griffin
*Assistant Examiner* — Cameron J Allen
(74) *Attorney, Agent, or Firm* — Curtis B. Behmann; Borden Ladner Gervais LLP

(57) ABSTRACT

A system for water purification, filtration and item sanitization are described herein. In one embodiment, a water filtration device uses an extruded carbon sheet or granulated activated carbon to filter unpurified, gravity-fed water. A filtering medium is provided within a lower opening of an upper reservoir for filtering unfiltered water passing therethrough, the filtering medium being located above and not extending into a lower reservoir. The device can be a stand-alone water container or incorporated within a water purification system having a further purification technology located in a base in fluid communication with the water container. The base can include controls for informing a user when the water filtration or item sanitization has been completed. Practical applications include drinking water filtration, sanitization of household items, medical equipment, and the like.

12 Claims, 12 Drawing Sheets

U.S. PATENT DOCUMENTS

| | | | |
|---|---|---|---|
| 4,123,800 A | 10/1978 | Mazzei | |
| 4,173,051 A | 11/1979 | Reid | |
| 4,290,791 A | 9/1981 | Matsui et al. | |
| 4,306,971 A | 12/1981 | Hankammer | |
| 4,495,043 A | 1/1985 | Marets | |
| 4,931,225 A | 6/1990 | Cheng | |
| 4,969,996 A | 11/1990 | Hankammer | |
| 5,048,404 A | 9/1991 | Bushnell et al. | |
| 5,061,406 A | 10/1991 | Cheng | |
| 5,178,799 A | 1/1993 | Brown et al. | |
| 5,218,304 A | 6/1993 | Kinlen et al. | |
| 5,225,078 A | 7/1993 | Polasky et al. | |
| 5,302,325 A | 4/1994 | Cheng | |
| 5,332,494 A | 7/1994 | Eden et al. | |
| 5,460,705 A | 10/1995 | Murphy et al. | |
| 5,503,809 A | 4/1996 | Coate et al. | |
| 5,520,893 A | 5/1996 | Kasting, Jr. et al. | |
| 5,643,444 A | 7/1997 | Garrigues et al. | |
| 5,690,978 A | 11/1997 | Yin et al. | |
| 5,693,226 A | 12/1997 | Kool | |
| 5,744,030 A | 4/1998 | Reid et al. | |
| 5,770,033 A | 6/1998 | Murphy et al. | |
| 5,824,243 A | 10/1998 | Contreras | |
| 5,846,418 A | 12/1998 | Thompson et al. | |
| 5,851,375 A | 12/1998 | Bodger et al. | |
| 5,863,128 A | 1/1999 | Mazzei | |
| 5,880,378 A | 3/1999 | Behring, II | |
| 5,882,613 A | 3/1999 | Gipson, II | |
| 5,893,641 A | 4/1999 | Garcia | |
| 5,927,304 A | 7/1999 | Wen | |
| 5,989,407 A | 11/1999 | Andrews et al. | |
| 6,019,031 A | 2/2000 | Qin et al. | |
| 6,030,586 A | 2/2000 | Kuan | |
| 6,086,932 A | 7/2000 | Gupta | |
| 6,093,432 A | 7/2000 | Mittal et al. | |
| 6,103,114 A | 8/2000 | Tanner et al. | |
| 6,135,279 A | 10/2000 | Dryer | |
| 6,171,625 B1 | 1/2001 | Denvir et al. | |
| 6,200,618 B1 | 3/2001 | Smith et al. | |
| 6,238,552 B1 | 5/2001 | Shannon | |
| 6,290,848 B1 | 9/2001 | Tanner et al. | |
| 6,368,472 B1 | 4/2002 | McGuire | |
| 6,379,628 B2 | 4/2002 | de Jong et al. | |
| 6,391,191 B2 | 5/2002 | Conrad | |
| 6,405,875 B1 | 6/2002 | Cutler | |
| 6,485,696 B1 | 11/2002 | Sato et al. | |
| 6,485,769 B2 | 11/2002 | Audy et al. | |
| 6,499,671 B1 | 12/2002 | Sands et al. | |
| 2002/0185423 A1 | 12/2002 | Boyd et al. | |
| 2003/0112012 A1 | 6/2003 | Mosley et al. | |
| 2004/0149643 A1* | 8/2004 | Vandenbelt et al. | 210/282 |
| 2006/0157399 A1* | 7/2006 | Vandenbelt et al. | 210/282 |

FOREIGN PATENT DOCUMENTS

| | | |
|---|---|---|
| DE | 3000828 | 7/1981 |
| DE | 3632446 A1 * | 3/1988 |
| DE | 19948923 | 8/2000 |
| DE | 10061297 | 6/2002 |
| GB | 2206292 | 1/1989 |
| JP | 5023682 | 2/1993 |
| JP | 8222353 | 8/1996 |
| JP | 10069962 | 3/1998 |
| JP | 10-180270 | 7/1998 |
| JP | 10230229 | 9/1998 |
| JP | 2002052301 | 2/2002 |
| WO | 92/16241 | 10/1992 |
| WO | 99/48588 | 9/1999 |
| WO | 02/42225 | 5/2002 |
| WO | 0248054 | 6/2002 |
| WO | 03/032773 | 4/2003 |

OTHER PUBLICATIONS

U.S. Appl. No. 60/431,128 Author: Vandenbelt, Rudy and Hamilton, Jeremy, Application Title: Pitcher Type Point of Use Water Purifier, Effective Filing Date: Dec. 5, 2002, Pertinent Pages: Whole Document.*

Office Action for U.S. Appl. No. 10/875,297, dated Oct. 31, 2008.

Office Action for European Patent Application Serial No. 04701335.4 dated Sep. 30, 2008.

Office Action for U.S. Appl. No. 10/875,297, dated May 28, 2009.

Office Action for Japanese Patent Application No. 2006-500432, dated Dec. 3, 2008.

U.S. Appl. No. 10/562,206, Notice of Allowance dated Dec. 14, 2009.

* cited by examiner

SYSTEM AND DEVICE FOR WATER FILTRATION AND PURIFICATION

CROSS-REFERENCE TO RELATED APPLICATIONS

This application is a divisional of U.S. patent application Ser. No. 10/562,206 filed Dec. 23, 2005, and issued as U.S. Pat. No. 7,708,958 on May 4, 2010,which is a 371 application of PCT/CA2004/000946, filed Jun. 25, 2004, which claims priority to and is entitled to the benefit of U.S. Provisional Patent Application 60/482,519 filed Jun. 26, 2003, and to International Applications PCT/CA2004/000042, with an international filing date of Jan. 12, 2004 and PCT/CA2004/00043, with an international filing date of Jan. 9, 2004, each of which is incorporated herein by reference.

FIELD

The present disclosure relates generally to a system and a device for water filtration and purification.

BACKGROUND

Microbial contamination is a primary cause of disease. Bacteria and viruses can be found in water, on food and on surfaces. Currently, there are several different technologies available to eliminate these contaminants from drinking water. However, the effectiveness of a particular method depends on the influent water and the type of microbe present.

Increased concern from the public on issues of water quality has resulted in an explosion of water filtration devices on the market, particularly for household use. A popular household water filtration device is in the style of a pour-through pitcher. Typically, unfiltered water is added to a basin at the top of the device. Through the action of gravity, water percolates through a filtering media (usually consisting of granulated activated carbon) located between the basin and a collection reservoir. Filtered water is then dispensed from the collection reservoir for drinking. For the general public, gravity-controlled pitcher-type water filtration systems are cost effective. Many such water filtration systems are provided under the Brita® brand name.

One limitation of this kind of device is the inability to filter out and destroy smaller organisms and microbes. To facilitate the flow of water, the filtering media through which water is drawn needs to be of a porous nature. Because of this necessity, such devices do not filter as effectively as other water treatment devices. Part of this inefficiency is caused by a lack of additional purification steps currently available in the prior art, such as ozonation, ultra-violet irradiation, and cell membrane electrofragmentation.

The filtering media or cartridge used in these pitcher-type filtering systems usually extends down into the collection reservoir, coming in contact with the filtered water. The porosity of the filter media promotes the infiltration, collection and growth of organisms. Thus, there is an increased potential for contamination of the filtered water.

The lack of additional purification steps limits the use of the filtered water produced by such prior art devices to drinking water purposes, as opposed to other potential applications for the use of purified or treated water.

U.S. Pat. No. 5,225,078 issued to Polasky et al., discloses a pour-through gravity-flow pitcher filter.

U.S. Pat. No. 6,103,114 issued to Tanner et. al., cites a device which attempts to avoid cross contamination by the design of the spout, pour area and seal between the inner reservoir and the filtered water reservoir. However, the filter in this design still extends into the filtered water reservoir and is a potential source of contamination.

U.S. Pat. No. 6,391,191 issued to Conrad discloses a domestic water treatment appliance with a pump which uses ozone and a carbon block filter to disinfect water, but does not utilize a pour-through filter prior to the ozonation process.

U.S. Pat. No. 6,238,552 issued to Shannon discloses a universal insert for a water purifier with filter on top and bottom and a guide for sliding into a pitcher.

U.S. Pat. Nos. 4,969,996 and 4,306,971 issued to Hankammer discloses a column-like filter device extending into collection reservoir and, thus, yields a potential source of contamination.

U.S. Pat. No. 6,290,848 issued to Tanner et al., discloses a porous particulate filter for removing 99.95% of all 3-4 μm cryptosporidium and other protozoan cysts. U.S. Pat. No. 6,103,114, also issued to Tanner et al., describes a carafe-style filter device with lip over the edge to prevent untreated water from mixing with treated water when pouring.

U.S. Pat. No. 6,405,875 issued to Cutler discloses a carafe-style filter device with an ion-exchange resin and carbon granules which removes 99.95% of all 3-4 μm particles. However, this device extends into filtered water reservoir and thus may be susceptible to contamination.

Thus, there is a need for a water filtration device that keeps the filtering media from being in contact with the filtered water. There is also a need for an effective drinking water filtration and purification system which takes advantage of different treatment methods. There is a further need for a purification or sanitization system and/or method that can be used to sanitize different items, while taking advantage of improved purification techniques.

SUMMARY

It is an object of the present disclosure to obviate or mitigate at least one disadvantage of previous drinking water filtration systems or devices.

The disclosure relates to a system in which a gravity-fed filter device is combined with a water purification technology to produce an overall system for filtration of water. In the case of the system, a gravity-fed filter may be an extruded carbon filter between fabric, a non-extruded carbon filter, or a fabric filter without any activated carbon. The gravity-fed filter is located above a filtered water reservoir. Preferably, the gravity-fed filter does not extend into the water within the filtered water reservoir. However, the system encompasses gravity-fed filters which extend downward into a filtered water reservoir, as well as those which do not. According to the disclosure, the system comprises a gravity-fed filter and a purification technology selected from the group consisting of a pair of electrodes; an ozonification means; ultra, micro and nanofiltration; an ultraviolet (UV) light source; and aeration/oxygenation. The purification technology is appropriately arranged so as to act on the water within the filtered water reservoir. Such a system may comprise a pitcher mounted on a base, or may be housed within a water cooler, a juicer, a coffee maker or any other device in which pre-conditioning of water is desirable. The system may be a portable unit. Further, the system may be a plumbed in system, where a float arrangement can be used to supply water to the gravity-fed filter.

The disclosure provides a water purification system comprising a water container, such as a drinking water filtration device, having an upper reservoir for receiving unfiltered water. The upper reservoir has a lower opening; a filtering medium within the lower opening of the upper reservoir for filtering unfiltered water passing therethrough; and a lower reservoir for receiving water passed through the filtering medium. The lower reservoir has a lower opening. Also, a base is included for receiving the water container, or drinking water filtration device, in fluid communication with the lower opening of the lower reservoir. The base comprises a purification technology for purification of water received from the lower reservoir. The system also includes a water circulator for circulating water between the lower reservoir and the purification technology within the base.

The present disclosure also allows gravity-fed filtration of water in a stand-alone filtration device using an extruded carbon filter which does not extend into the water that has passed through the filter. As a stand-alone filtration device, an extruded carbon filter is located above a filtered water reservoir, and may be disposed between an upper and a lower fabric sheet. The filter does not extend into the filtered water reservoir. Thus, once water passes through the filter and into the filtered water reservoir, there is no further contact with the filter. Such a stand-alone filtration device can be a pitcher, a water cooler, a juicer, a coffee maker or any other device in which pre-conditioning of water is desirable. The device may be a portable unit, or may incorporate a plumbed in unit, where a float arrangement is used to feed the filter.

The disclosure provides a water container, such as a drinking water filtration device, comprising an upper reservoir for receiving unfiltered water; the upper reservoir having a lower opening. A filtering medium is also included, located within the lower opening of the upper reservoir for filtering unfiltered water passing therethrough. The filtering medium is selected from the group consisting of: a granulated activated carbon (GAC) cartridge; an extruded carbon sheet between layers of fabric material; and an ion exchange resin. Also, a lower reservoir is included for receiving water passed through the filtering medium. The filtering medium is located above and not extending into the lower reservoir.

An aspect of the disclosure provides a method of sanitizing items, comprising: providing the items and unsanitized water in a sanitizing container, the sanitizing container being in removable fluid communication with a sanitizing base unit; and treating the unsanitized water with the items in the sanitizing container, the step of ozonating including sanitizing the items as the water is being treated. The step of treating the unsanitized water can include ozonating the unsanitized water. The step of treating the unsanitized water with the items in the sanitizing container can include: a) drawing water from the sanitizing container via a pump, b) pumping water from (a) through a purification technology in the base unit, and c) directing water from (b) back into the sanitizing container.

Another aspect of the disclosure provides a sanitizing container for sanitizing items, the sanitizing container for use with a sanitizing base unit, the sanitizing container comprising: an outer container including a fluid transfer valve for removable fluid communication with the sanitizing base unit; and an item container for mating with the outer container, for receiving items to be sanitized.

A further aspect of the disclosure provides an item sanitizing system comprising: a container having a fluid transfer device and having an item holder for holding items in the container for sanitization; a base for receiving the container in removable fluid communication with the fluid transfer device, said base comprising a purification technology for purification of water received from the container; and a water circulator for circulating water between the container and the purification technology. The water circulator comprises a pump, connections, and electronic controls. The electronic controls can comprise an auto-sensing circuit which detects the presence of the filtration device on the base, activates an appropriate program, and illuminates a ready light. The program can be initiated when a user pushes a start button when said ready light is illuminated. The program can comprise a treatment period controlled by time and/or concentration, said treatment period consisting of: a) drawing water from the lower reservoir via a pump, b) pumping water from (a) through the purification technology, c) directing water from (b) back into the lower reservoir; and d) communicating to the user via a light and/or audible alarm indicating that the container can be removed from the base.

Other aspects and features of the present disclosure will become apparent to those ordinarily skilled in the art upon review of the following description of specific embodiments of the disclosure.

DETAILED DESCRIPTION

A system for water purification, filtration and item sanitization are described herein. In one embodiment, a water filtration device uses an extruded carbon sheet or granulated activated carbon to filter unpurified, gravity-fed water. A filtering medium is provided within a lower opening of an upper reservoir for filtering unfiltered water passing therethrough, the filtering medium being located above and not extending into a lower reservoir. The device can be a stand-alone water container or incorporated within a water purification system having a further purification technology located in a base in fluid communication with the water container. The base can include controls for informing a user when the water filtration or item sanitization has been completed. Practical applications include drinking water filtration, sanitization of household items, medical equipment, and the like.

Embodiments of the present disclosure provide a sanitization system that allows the sanitization or disinfection with a multitude of applications, such as a safe method for the consumer to sanitize or disinfect water economically and on site with a single unit. Further, foods, vegetables, plants, and surfaces with which a number of people regularly come into contact benefit from an effective sanitization system according to an embodiment of the present disclosure that does not employ dangerous chemical agents.

As used herein, the term sanitization refers to removal of at least a portion of an unwanted component from a substance, such as from a liquid, for example water, or from a solid, for example an object, a surface or a food product. The term purification, when used in reference to water or other liquids, is used synonymously herein with the term sanitization. As used herein, the term disinfection refers to a high level of sanitization of either a liquid or a solid. At the level of disinfection, the vast majority of live bacteria, viruses and/or other "infective" agents are removed from a liquid or a solid. Disinfection is not, however, used synonymously with the term sterilization, which is a high form of sanitization, implying a process more complete than disinfection.

Figure 1:
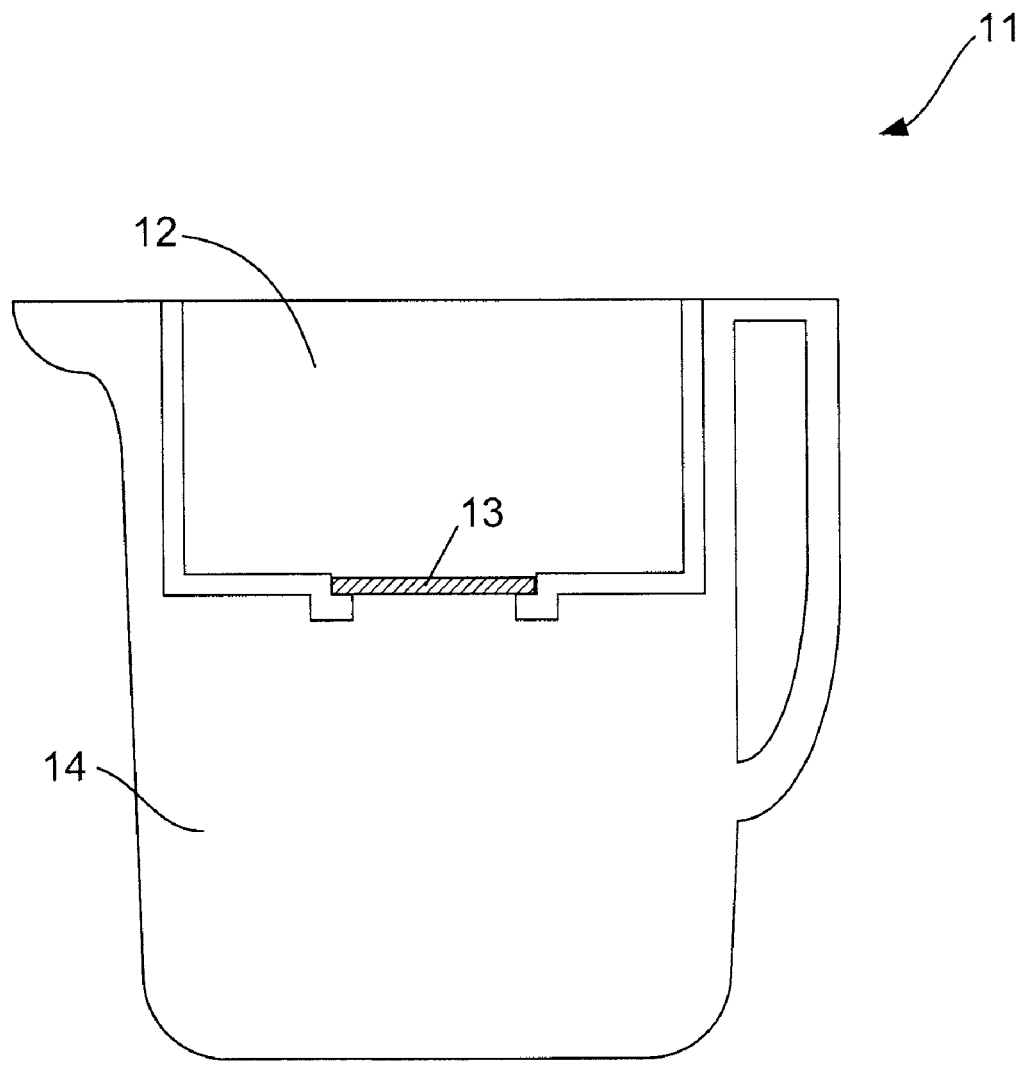
FIG. 1 shows a schematic representation of a drinking water filtration device according to the disclosure.

FIG. 1 schematically illustrates an embodiment of a device according to the disclosure. The device comprises a water container 11 and filtering media 13. Unfiltered water is added to an upper reservoir 12 at the top of the container, which in this case is shown as a pitcher. Water is gravity-fed through the filtering media which is located within the upper reservoir at the top of the container. Thus, the filtering media is not in contact with water already filtered, which has passed through into the lower reservoir 14. When used as a stand-alone device, the filtering media preferably comprises an extruded carbon sheet between the layers of fabric material. In other embodiments, especially when the device is part of a system, the filtering media may comprise a cartridge of granulated activated carbon (GAC), an extruded carbon sheet between the layers of fabric material, an ion exchange resin with or without a GAC or extruded carbon sheet, or one or more layers of fabric material without carbon for prefiltration purposes. In this schematic illustration, water is gravity-fed through the filtering media and is held in the lower reservoir until use.

In other words, an embodiment of the present disclosure provides a stand-alone drinking water purification device. The device includes an upper reservoir for receiving unfiltered water, the upper reservoir having a lower opening. The device also includes a filtering medium within the lower opening of the upper reservoir for filtering unfiltered water passing therethrough, the filtering medium being selected from the group consisting of: a granulated activated carbon (GAC) cartridge; an extruded carbon sheet between layers of fabric material; and an ion exchange resin. The device also includes a lower reservoir for receiving water passed through the filtering medium, the filtering medium being located above and not extending into the lower reservoir. The device can be a pitcher, and the water can be gravity-fed through said filtering media.

Figure 2:
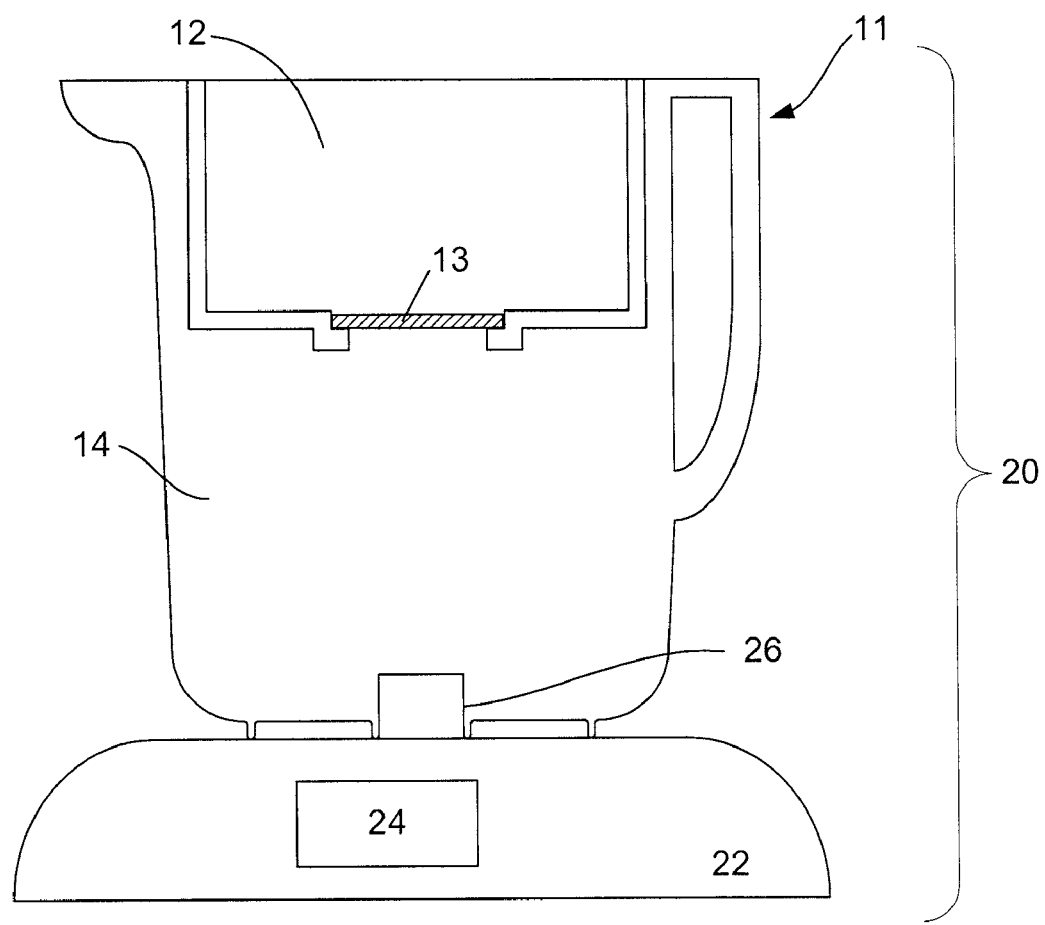
FIG. 2 shows a schematic representation of a water purification system according to the disclosure.

FIG. 2 schematically illustrates an embodiment of the system of the disclosure in which the filtration device is used in combination with another purification technology. In this case, the water container 11 is a removable component of a multi-technology water filtration system 20. The container rests on a base 22. The base contains a pump, an ozone contacting device, connections, electronic controls or control electronics, and a purification technology 24 comprising at least one of a variety of purification technologies. The ozone contacting device, or mixing device, can be implemented in any number of ways. One implementation of the ozone contacting device is as a venturi, such as a vortex-venturi. Another implementation of the ozone contacting device is as a sparger and ozone pump. Specifically, in the venturi implementation, this aspect of the disclosure allows mixing of fluids based on the venturi principle, and in a particular implementation can introduce a vortex component for accelerated entry of a main fluid into the device prior to mixing with an additive fluid.

The purification technology may be selected from: i) a pair of electrodes, ii) an ozonification means (having an ozone generator, an ozone destructor and a centrifugal degasser), iii) filtration (one or more of ultra, micro, or nanofiltration), iv) an ultraviolet (UV) light source, and v) aeration/oxygenation which can incorporate a sparger type media for releasing bubbles and optionally, a plastic deflector can be used to aid in circulation in the embodiments for which aeration/oxygenation is used as a purification means. Aeration can be used alone simply to alter aesthetic qualities of water. A fluid transfer port or valve, such as a double check valve, 26 is located at the interface of the water container and the base to ensure appropriate flow of water.

In this system, electronic controls such as control electronics within the base can incorporate an auto-sensing circuit to detect the presence of the water container on the base, and can activate an appropriate program depending on whether the container is present or absent. A user can activate the purification technology by pressing a button.

The pump within the base draws water from the lower reservoir and pumps it through an ozone contacting device. In the case where ozone purification is the purification technology employed and the ozone contacting device is a venturi, the venturi has a gas inlet which draws air through an ozone generator. The venturi in the base imparts a rotary motion to the entire flow and creates an annular flow through the injection portion causing a larger portion of the flow to reach high velocity and a larger portion of the flow to directly contact the secondary fluid.

A centrifugal gas-liquid separator may be used with the base, which includes an integrated gas release valve. This separator allows the removal of entrained gasses from a liquid flow. A liquid-gas mixture is injected tangentially into a helical channel which initiates a high velocity vortex. The vortexing liquid-gas mixture rises up the tube and under centrifugal force the gas is forced to the centre of the vortex and the liquid is forced to the periphery. As the liquid-gas mixture rises in the tube, a slot around the tube draws off a portion of the liquid, which is discharged through the outlet. The remaining liquid-gas mixture rises into the valve chamber. The liquid level in the valve chamber interacts with a float that opens and closes a port releasing the gas as needed.

In one embodiment, the ozone generator may be a corona-discharge type, and converts a portion of the oxygen in the air into ozone. The ozone is mixed with the water in the venturi. The water ozone mixture then passes into a centrifugal degasser, which removes the air and undissolved ozone. The removed gas is directed to an ozone destructor, which converts ozone into oxygen and safely releases it into the atmosphere.

In another embodiment of the system according to the disclosure the base may incorporate an electric field created across a pair of electrodes as the purification technology. In this embodiment, purification may proceed by creating a voltage potential across the membrane of a single organism, for example a potential of 1 volt. The voltage potential causes the membrane to rupture and effectively killing the organism.

In a further embodiment, the base contains a purification technology employing a membrane of either ultra, micro or nanofiltration. The membrane has an effective opening, and organisms (such as those found in drinking water) are trapped by the membrane structure and removed from the drinking water.

In yet another embodiment, the base contains an ultraviolet (UV) light source as the purification technology. In this embodiment, UV light is passed over water which has flowed out by a pump or other means from the lower reservoir of the water container, and back into the lower reservoir of the container.

In yet another embodiment, the base contains a venturi which draws in atmospheric oxygen or pure oxygen to aerate and/or oxygenate the water. In this case, aeration/oxygenation is the purification technology employed. This aeration and/or oxygenation purification may also employ a sparger system in the base of the container.

Regardless of the selected purification technology, the system pumps water through the purification means, and water is then is directed back into the lower reservoir. The cycle may be allowed to continue until a predetermined time or purity is reached. A light and/or audible alarm may be employed to indicate to a user when the purification process is complete, and that the container can be removed.

The system according to the disclosure incorporates a fluid transfer port or valve 26 at the interface of the water container and the base, which allows the container to be removed without leaking. The fluid transfer valve assembly, or fluid control port or liquid interface, according to the disclosure allows the control of fluids, and in particular, but not limited to, the control of fluids into and out of a container. The container may be permanently mounted or removable and the flow into and out of the container may occur simultaneously or sequentially. The fluid transfer valve can be implemented in any number of ways, such as by way of separate check valves for inflow and outflow, or a single double check valve for both inflow and outflow. The double check valve arrangement allows water to flow out of and into the container simultaneously while using a single connection point. Water flows from the lower reservoir of the container via a pump (or similar means), through an ozone contacting device such as a venturi, through the purification technology and back into the lower reservoir of the container. The particular embodiment of a double check valve is described in more detail below, although it is to be understood that any fluid transfer valve can be used according to embodiments of the present disclosure.

Figure 3:
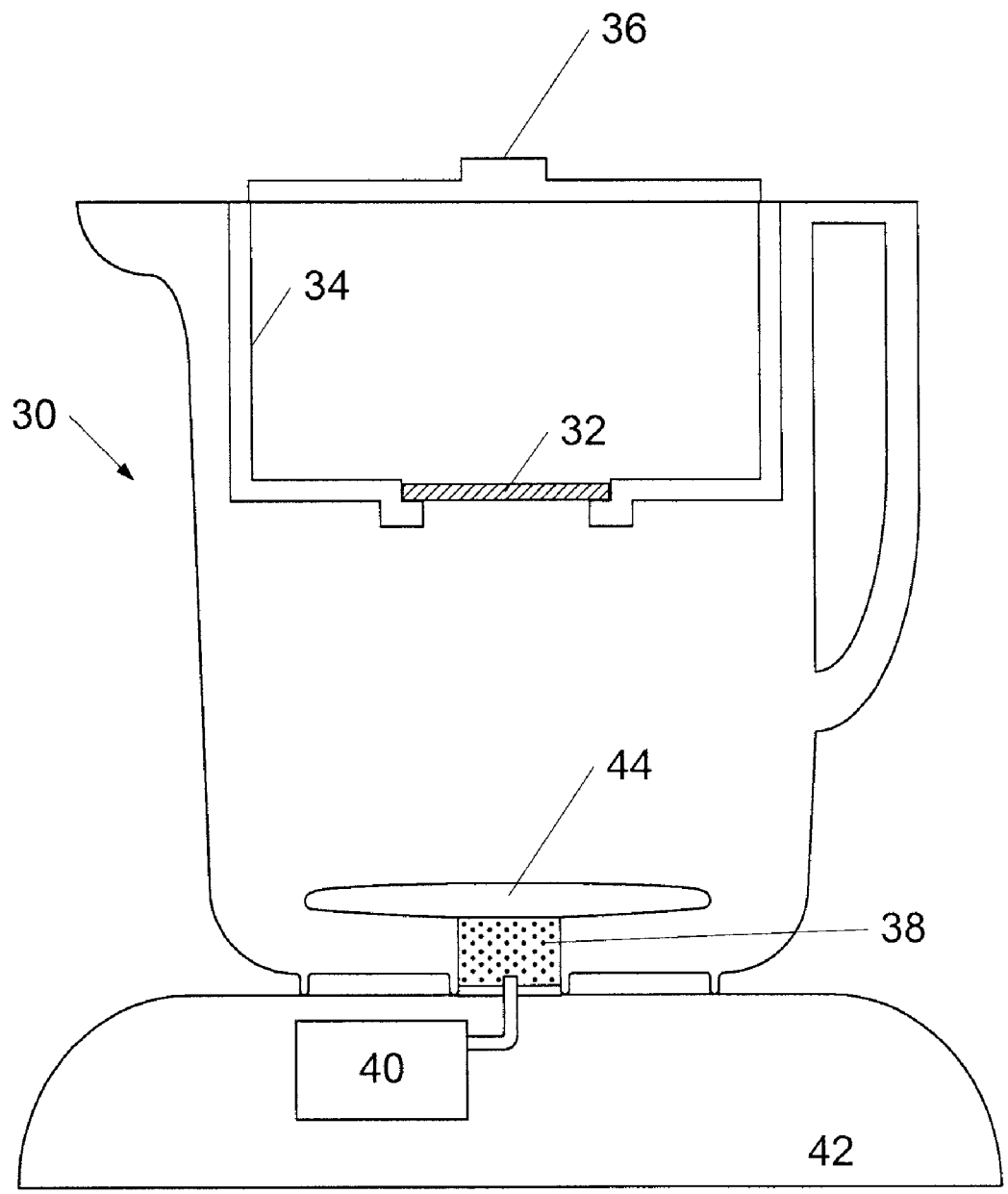
FIG. 3 is a front view of a pitcher located on a base according to an embodiment of the disclosure.

FIG. 3 illustrates a front view of an embodiment of the system according to the disclosure in which a water container such as a pitcher 30 has a flat extruded carbon sheet 32 between fabric as a filter media. The extruded carbon sheet is located in the floor of an upper reservoir 34. A lid 36 is provided to cover the upper reservoir. Water received in the upper reservoir 34 slowly filters through the extruded carbon sheet 32 and runs through into lower reservoir of the pitcher. A sparger medium 38 is located within the lower reservoir at the bottom of the pitcher, and is adapted for communication with an air pump 40. The pitcher is adapted to sit in a specific location on a base 42 through which the air pump 40 provides air. The air pump provides air to the sparger medium, thereby releasing bubbles into the water held within the pitcher, allowing purification of water. In this embodiment, a plastic reflector 44 is disposed above the sparger medium to aid in circulation of bubbles. In practice, this allows purification of water both by filtration through the extruded carbon filter and by aeration/oxygenation through the pump located in the base with which the pitcher communicates. Similar to the schematic shown in FIG. 2, a fluid transfer valve or port such as a double check valve can be used with this embodiment to ensure that appropriate flow of water into and out of the pitcher is accomplished. Electronic controls may be used within the base to allow detection of the pitcher on the base.

The embodiment of FIG. 3 shows a sparger provided in, or integral with, the water container. Such a water container can be re-usable, or can be a single-use water container. In an additional embodiment of the present disclosure, the water container can include all of the purification technology that is typically included in the base. This may be advantageous in some instances when drinking water purification is the only anticipated use for such a water container. Of course, the embodiment including a water container for removable fluid communication with the base provides for alternative uses of containers with the same base, as will be discussed later.

A fluid transfer valve according to an embodiment of the present disclosure can include any liquid interface, such as a fluid communication port, fluid control port, fluid transmission port, fluid transfer port, and the like. The fluid transfer valve assembly according to the disclosure allows the control of fluids, and in particular, but not limited to, the control of fluids into and out of a container. The container may be permanently mounted or removable and the flow into and out of the container may occur simultaneously or sequentially.

The fluid transfer valve can be implemented in any number of ways, such as by way of separate check valves for inflow and outflow, for example an influent valve and an effluent valve, or a single double check valve for both inflow and outflow. Check valves are used in a variety of applications where fluid flow needs to be restricted in one direction. Examples include the filling and emptying of tanks and the control of fluid flow in conduits such as pipes. However, if flow is required in two directions simultaneously, for example flow into and out of a tank, two separate check valves are required, and thus two openings are required in the tank.

According to an embodiment of the disclosure, there is provided a fluid transfer valve, for example a double check valve, which allows two independent flows to occur simultaneously or independently. In the case of the double check valve, these independent flows pass through the same check valve assembly. The double check valve embodiment will be described in further detail below.

The double check valve allows two independent flows to occur either simultaneously or alternately through the same check valve assembly.

The double check valve allows two separate and independent flows to occur through a single check valve assembly. In addition, devices such as caps can be added to improve flow separation and improve mixing through the use of flow diverters that impart rotational flow. Also, the check valve assembly can allow the tank to be removed from an interface and prevents the fluid from leaking from said tank. The two valve stems within the check valve assembly can be operated independently or co-operatively.

The double check valve may include a first and second check valve operated independently and having first valve contained within the second. Two independent fluid flow paths are thus created, one flowing through the second valve stem and around the first, and a second flow around the second valve stem.

According to one embodiment, the double check valve assembly includes an outer body having an inlet and an outlet with the first and second valve stems contained in said outer body. The outlet of the outer body is the valve seat to said second valve stem. The first valve stem is smaller than said second valve stem, and is contained within the second valve stem and operated along a common axis. The second valve stem has a cylindrical conduit passing through it in which the first valve stem is contained, and also contains the valve seat for said first valve stem. Fluids can thus pass around the first valve stem and through the second. Individual springs surround the first and second valve stems. These springs act on the valves to engage their respective valve seats. The first and second valve stems can be actuated independently or co-operatively.

When the valves are open, two independent fluid flows are created, one flow around the second valve stem and through the outlet in the outer body, and one through the second valve stem and around the first valve stem.

The double check valve assembly according to this embodiment may optionally have an outer body formed of any type of container, such as a tank either permanently mounted or mobile, requiring the control of the input and/or output of a fluid.

The first valve stem may optional have a cylindrical conduit formed partially through it allowing fluids to pass through the conduit when the first valve stem is unseated from its valve seat.

The outer body may optionally incorporate one or more protrusions that are arranged radially and surround the outlet and the first and second valve stems. These protrusions may take the form of mounting bosses or flow diverters. In the case where the protrusions are flow diverters, these may be configured to impart a rotation motion to the fluid exiting around the second valve stem. In the case where the protrusions are mounting bosses, such mounting bosses are used to mount a removable cap to the outer body and over the first and second valve seats. In such an embodiment, the cap may contain flow diverters, a centrally located conduit and a valve seat.

The cap may be mounted to the mounting bosses, in which case the flow diverters contained in the cap create channels through which fluid will flow. The flow diverters may impart a rotation motion to the fluid. When the first and second valve stems are open the second valve stem seats against the valve seat in the cap and the first valve seat passes into the conduit formed through the center of the cap. Thus two flow paths are effectively divided. One flow around the second valve stem, under the cap and through the flow diverters and the other flow through the conduit in the center of the cap and around the first valve stem.

Figure 4:
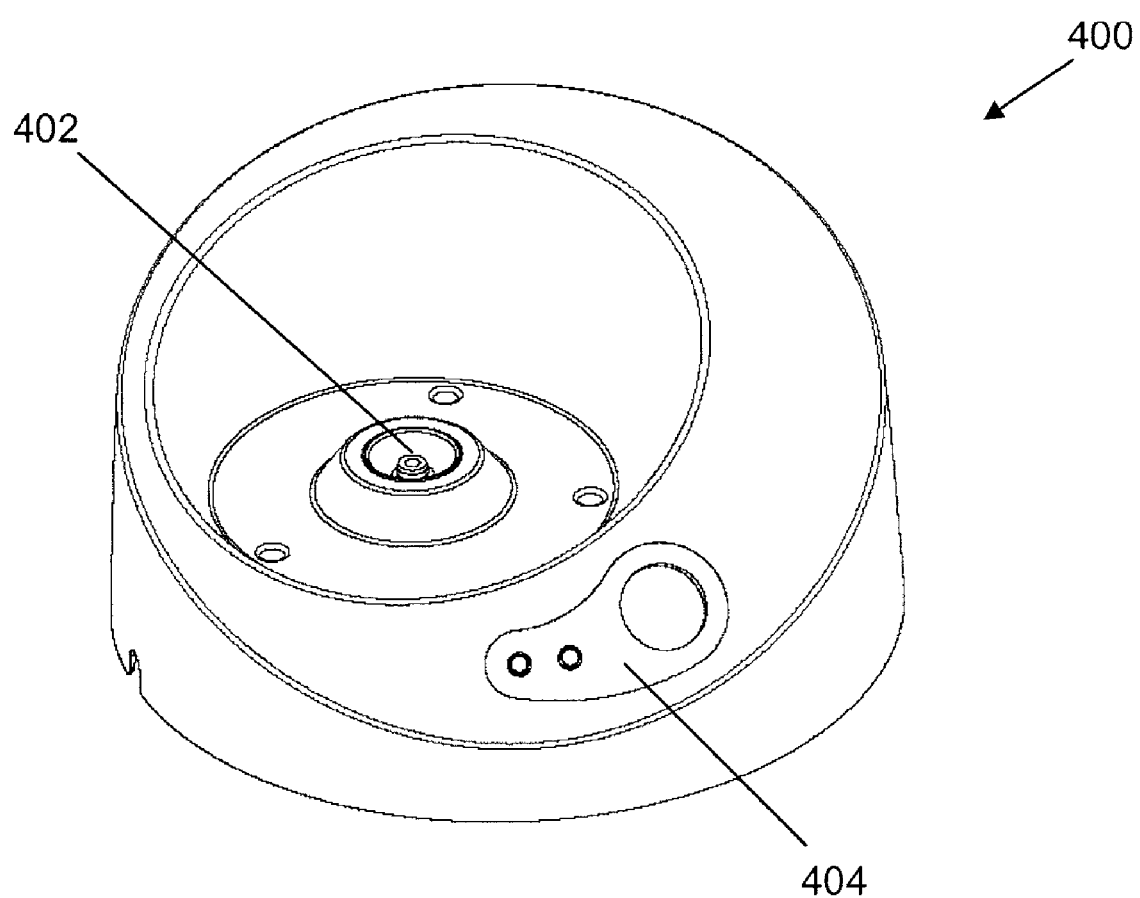
FIG. 4 is a perspective view of a base unit of a sanitization system with which a water purification system, or any other container, according to embodiments of the disclosure can be interfaced.

FIG. 4 is a perspective view of a base unit of a sanitization system with which a water purification system, or any other attachment, according to embodiments of the disclosure can be interfaced. The base unit 46 of FIG. 4 can be similar to the base units 22 and 42 of FIGS. 2 and 3, respectively, but need not be identical to those base units. The base includes a mating component (402) to interface with a fluid transfer valve present on the bottom of a container. A control button display pad (404) is preferably provided and is illustrated on a forward-facing portion of the base, which is accessible to a user. The control button display pad can include any number of controls or display windows. Such controls or display windows may include but are not limited to an on/off button, a program selection button, a "ready" light to indicate to a user when the liquid in a container has been adequately processed, or any type of read-out display that will advise a user of an appropriate message. One skilled in the art could easily determine other types of controls or display windows to include on the pad. In this embodiment, the processing components are sized to be housed within the base in a compact manner that allows for counter-top placement or installation of the unit. However, it is to be understood that the components need not be housed within a base per se, for example, in scaled-up systems that represent permanent installations.

A container (or plurality of containers) provided according to an embodiment of the present disclosure may be either removable or fixed within the system. In the case where the container is integral (and not readily removable) from the system, it may be present in the form of a holding tank. This type of container may be applicable for larger-scale designs where a user would not necessarily require the container to be portable. However, for a small scale or residential applications, it may also be desirable to have a fixed-position, non-removable container from which aliquots of ozonated water can be drawn, for example through a tap, or via a conduit to a select appliance.

According to one embodiment, the system includes a plurality of removable containers. Of course, the system of the disclosure only requires one container, and it need not be removable. The embodiment in which more than one container is provided, and the containers are removable is discussed hereinbelow. In this embodiment, the control electronics incorporate an auto-sensing circuit, to detect which type of fluid container is connected to the base and to activate an appropriate program. For example, if a fluid container is sensed that is required for drinking water, a lower level of ozonation may be desired. Alternatively, if a fluid container is sensed that may be used for cleaning of surfaces, a higher level of ozonation may be desired.

As an alternative to an auto-sensing circuit, a user may select the appropriate cycle. The treatment period may be controlled manually, or can be set to automatic control based on time and/or ozone concentration in the resulting water. In an embodiment where control is based on ozone concentration, the system can include a sensor to detect the ozone level in the water that is being ozonated, and a means by which to impart the sensed level to the control electronics and optionally convey that information to a display means.

Optionally, as described earlier, a container may take the form of a water pitcher for potable water sanitization. The container may also take the form of a bowl and strainer for sanitizing fruits and vegetables. Alternatively, the container may take the form of a spray bottle to contain ozonated water to be applied to surfaces, or of a reservoir and pad for cleaning surfaces. The container may also take the form of an inner and outer container for sanitizing small objects such as dentures, infant pacifiers etc. Also, the container may be a decanter to contain ozonated water when a larger quantity is required. Examples include pouring over foods such as meat, to rinse utensils or hands.

The sanitization system has a variety of applications both in residential and personal use, and for industrial and/or medical use. Examples of these include: preparation of purified drinking water or formation of ozonated drinking water for sanitization of objects or surfaces. Ozonated water formed with the sanitization system may be used to treat medical conditions, such as acne (having bacterial-related origins), foot fungus, sanitization of cuts, topical medical treatments for skin, cleaning of medical devices. Industrial uses for the food preparation industry may employ ozonated water formed according to the disclosure. For example, commercial use in cleaning surfaces in restaurants, food processing plants (such as meat processing plants), food packaging plants, such as factories, in supermarkets where produce is required to be kept fresh. Shelf-life of fresh produce may be extended by periodic spraying with ozonated water formed according to the disclosure. Employees may benefit from access to ozonated water for hand-washing in an industrial or public setting. Plants and flowers may be sprayed or watered with ozonated water formed according to the disclosure.

For home use, vegetables and fruits may be rinsed in a container in the form of a bowl and strainer and optionally including a lid, the container being attached to the base. For oral care, ozonated water so formed can be used to clean teeth, toothbrushes, or as a mouth rinse. Home wound care could incorporate the ozonated water in lieu of stronger solvents such as rubbing alcohol or hydrogen peroxide. As a deodorizer, the ozonated water so formed can be used to spray surfaces or interior surfaces, such as shoes.

Additionally, for home use, the system can be installed either as a counter-top model, or as an upstream built-in unit supplying water to home appliances. By using ozonated water for clothes washing or dish washing, the amount of detergent required can be reduced or eliminated.

Many other industrial and residential applications can be envisaged by one of skill in the art, and these fall within the scope of the disclosure.

FIGS. 5-8 illustrate examples of containers that can be used according to an embodiment of the present disclosure with a base unit such as the base 46 in FIG. 4. These containers make use of the fact that water purified by the purification means in the base unit can not only be suitable for drinking water, but in the case of ozonated water can be used as a cleaner or sanitizer, for example in the household environment.

Figure 5:
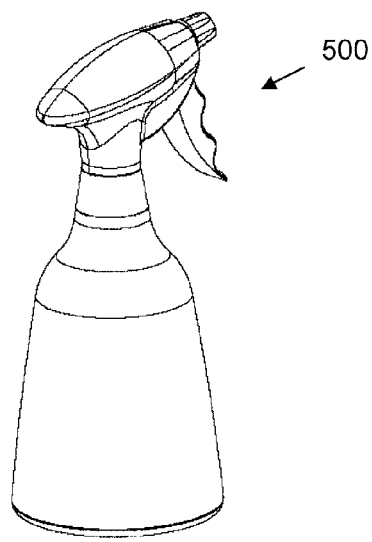
FIG. 5 illustrates a spray bottle that can be used with the base unit of FIG. 4 according to an embodiment of the present disclosure.

FIG. 5 illustrates a spray bottle (500) that can be used with the base unit of FIG. 4 according to an embodiment of the present disclosure.

Figure 6:
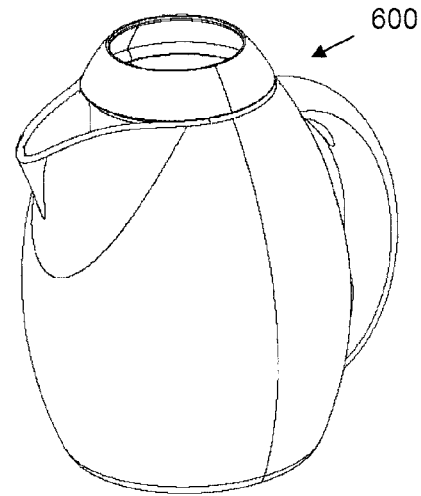
FIG. 6 illustrates a carafe that can be used with the base unit of FIG. 4 according to an embodiment of the present disclosure.

FIG. 6 illustrates a carafe (600) that can be used with the base unit of FIG. 4 according to an embodiment of the present disclosure.

Figure 7:
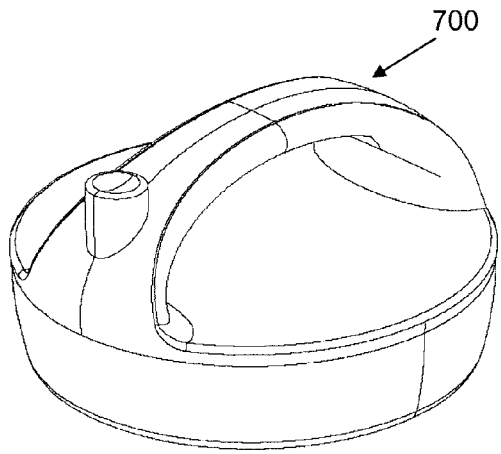
FIG. 7 illustrates a reservoir and pad for cleaning surfaces that can be used with the base unit of FIG. 4 according to an embodiment of the present disclosure.
Figure 8:
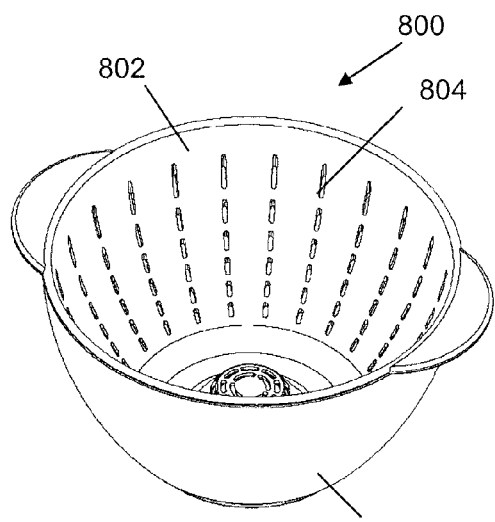
FIG. 8 illustrates a strainer and bowl that can be used with the base unit of FIG. 4 according to an embodiment of the present disclosure.

FIG. 7 illustrates a reservoir and pad (700) for cleaning surfaces that can be used with the base unit of FIG. 4 according to an embodiment of the present disclosure FIG. 8 illustrates a container (800) including a strainer and bowl that can be used with the base unit of FIG. 4 according to an embodiment of the present disclosure. The strainer (802) is shown as the internal portion of the container, having openings therein (804) for liquid to pass through and into the bowl (806), which is shown as the external portion of the container. A liquid interface (808) such as a fluid transfer valve can be seen at the bottom of the container through which water flows in order to enter and exit the container. This interface is in fluid communication with the double check valve, disposed on the bottom of the container (not shown). The container can optionally include a lid (not shown). The lid itself can define or have openings therein, to produce a lid strainer, which can be removably attached to the bowl, by mating components, a locking mechanism, or any other suitable means. The use of such a strainer lid is beneficial in straining the water back out of the container after purification or sanitization of the items in the container, without having to remove the strainer from the bowl.

Another example of a container that can be used according to an embodiment of the present disclosure is a container that is for subsequent use with a floor cleaner, which sanitizing container can be used with the base unit of FIG. 4 according to an embodiment of the present disclosure. Many simple mechanical household floor cleaners, such as the Swifter® WetJet® floor cleaner use an attachment or container for holding a detergent-based cleaner, and/or uses scrubbing strips, a cleaning pad, or the like to perform the sanitizing action separate from the liquid being used to clean floors. Embodiments of the present disclosure provide a container for mating with a floor cleaner, the container also for use with a base unit for providing ozonated water as a cleaning fluid. Not only is the use of such a sanitizing container more cost-effective since detergent does not need to be purchased and pads and strips do not need to be replaced. The container according to an embodiment of the present disclosure can be adapted for use with many different types of floor cleaning devices. Users can place regular tap water into the sanitizing container, have the water ozonated by placing the container on the base unit sanitizing system, and create their own floor cleaning fluid.

In addition to the containers described in relation to FIGS. 5-8, there are other attachments, or sanitizing containers, that can be used according to embodiments of the present disclosure. These sanitizing containers are for sanitizing items, and are for use with a sanitizing base unit, such as the base unit of FIG. 4. The sanitizing container comprises an outer container having a fluid transfer valve, or fluid transmission port, for removable fluid communication with the sanitizing base unit. The sanitizing container also comprises an item container for mating with the outer container, for receiving items to be sanitized. The sanitization can be achieved using a base unit that uses any number of purification or sanitization technologies, as have been described above, and as are known to those of ordinary skill in the art.

Similarly, there is provided according to an embodiment of the present disclosure an item sanitizing system, including a sanitizing container as described above. Specifically, the sanitizing system comprises a sanitizing container having a fluid transfer port and having an item container for holding items in the sanitizing container. The sanitizing system also includes a base for receiving the sanitizing container in removable fluid communication with the fluid transfer port, the base comprising a purification technology for purification of water received from the sanitizing container, and a water circulator for circulating water between the sanitizing container and the purification technology.

Figure 9:
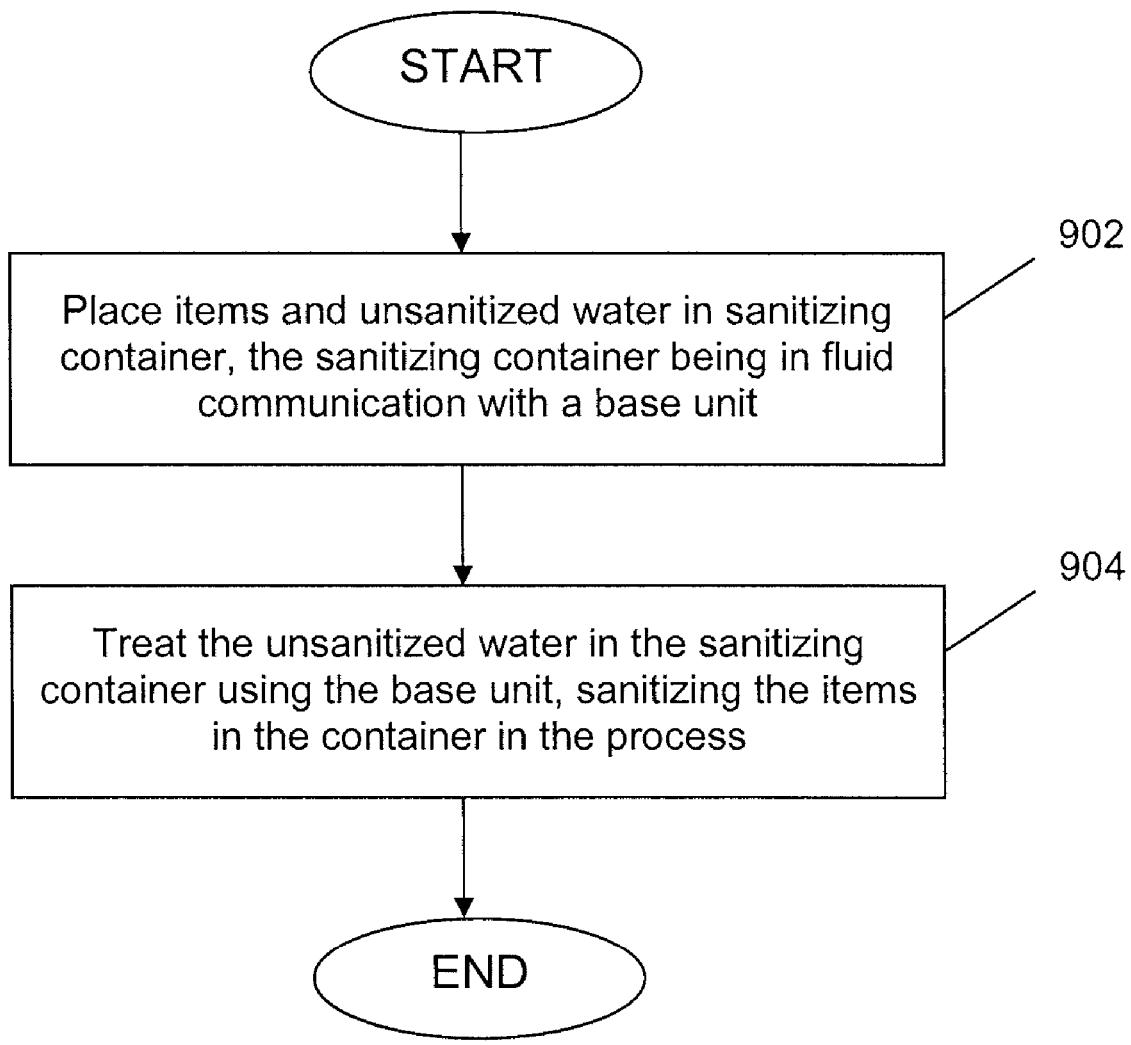
FIG. 9 is a flowchart illustrating a method of sanitizing items according to an embodiment of the present disclosure.

FIG. 9 is a flowchart illustrating a method of sanitizing items according to an embodiment of the present disclosure. Essentially, the method covers any method of using treated water, such as ozonated water or any type of purified or sanitized water, to sanitize items that have been placed in a sanitizing container such as those used in conjunction with embodiments of the present disclosure. The method includes the steps of: (902) placing the items and unsanitized water in a sanitizing container, the sanitizing container being in removable fluid communication with the sanitizing base unit; and (904) treating, or ozonating, the unsanitized water, the step of treating including sanitizing the items as the water is being treated.

It is to be understood that the step of treatment can include any of the purification steps currently available in the prior art, such as ozonation, ultra-violet irradiation, and cell membrane electrofragmentation. In particular, the step of treating can include: (a) drawing water from the container via a pump in the base unit; b) pumping water from (a) through the purification technology in the base unit; and c) directing water from (b) back into the container. Of course, when used with sanitizing containers according to embodiments of the present disclosure, the method can also include safely removing the sanitized items from the sanitizing container, in such a way as minimizes contamination during removal. This may depend on precautions taken by the user, but the structures used in the sanitizing containers according to embodiments of the present disclosure facilitate the ability to safely remove the items while reducing contamination, at least to the "operational" or functional parts of the items that are being treated or sanitized.

In this method, electronic controls such as control electronics within the base can incorporate an auto-sensing circuit to perform the step of detecting the presence of the water container on the base, and activating an appropriate program based on whether the container is detected as being present or absent. A user can activate the purification technology by pressing a button.

Regardless of the selected purification technology, the system pumps water through the purification means, and water is then is directed back into the lower reservoir. The cycle may be allowed to continue until a predetermined time or purity is reached. A light and/or audible alarm can be employed to perform a step of indicating to a user when the purification process is complete, and that the container can be removed.

Figure 10:
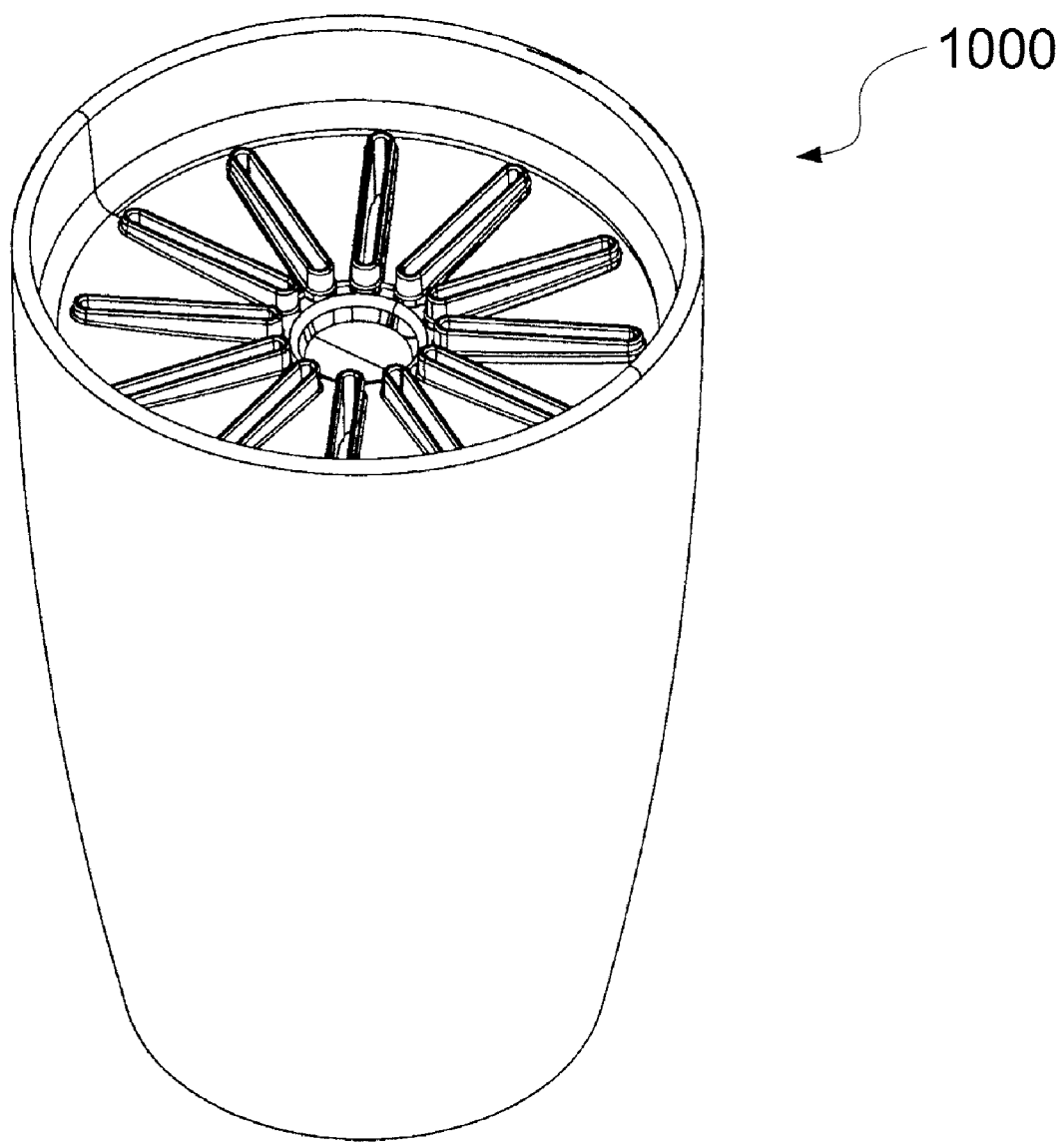
FIG. 10 illustrates a sanitizing container according to an embodiment of the present disclosure for sanitizing knives, which can be used with the base unit of FIG. 4.

FIG. 10 illustrates an sanitizing container (1000) for sanitizing knives according to an embodiment of the present disclosure that can be used with the base unit of FIG. 4. The sanitizing container (1000) can include an outer container, and an upper tray for mating with the outer container, the upper tray for receiving knives to be sanitized.

Figure 11:
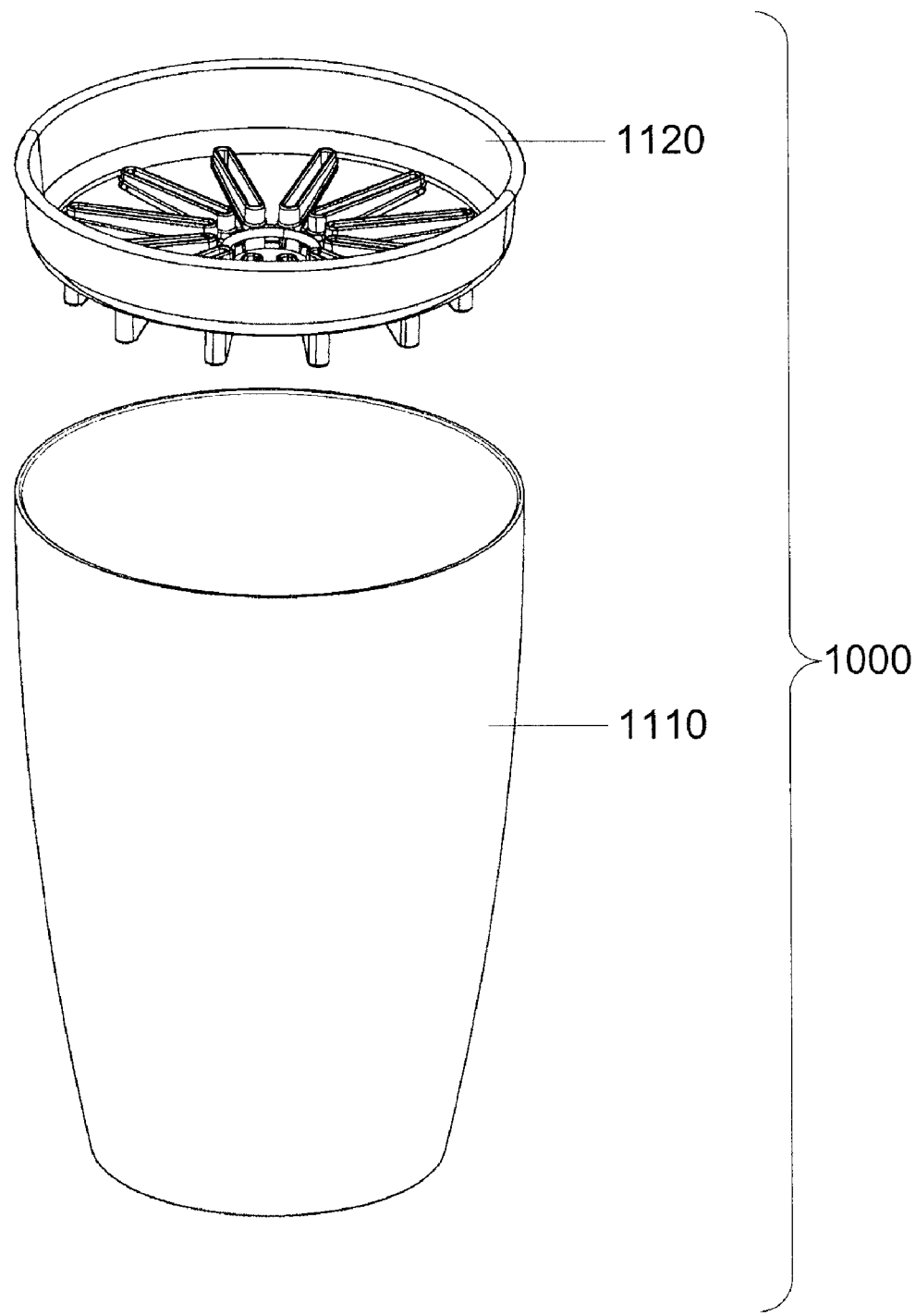
FIG. 11 illustrates an exploded view of the sanitizing container of FIG. 10.

FIG. 11 illustrates an exploded view of the sanitizing container of FIG. 10. The sanitizing container (1000) can comprise an outer container (1110) having an open top and a closed bottom, the outer container preferably being substantially cylindrical, optionally being tapered towards either the bottom or the top. The sanitizing container can also comprise an upper tray (1120), for mating with the open top of the outer container. A particular embodiment of the upper tray (1120) is shown as having a sidewall for mating with the inside of the outer container, and a lip for mating with the top of the outer container. A base of the upper tray is also shown as being provided near and joined with the bottom of the sidewall of the upper tray. The base of the upper tray defines and/or includes a plurality of knife receiving means. It is to be understood that many different embodiments and structures of an upper tray are possible, other than the one shown in FIG. 11.

Each of the knife receiving means can include a knife receiving structure, which defines a knife receiving slot. Although the knife receiving structures are shown in FIG. 11 to be substantially similar in size and in a particular configuration, it is to be understood that the knife receiving structures can be arranged in any shape or manner. In fact, a plurality of interchangeable upper trays can be provided, each upper tray having knife receiving means shaped and constructed so as to receive various types and sizes of knives. Also, although the knife receiving structures are shown in FIG. 11 to extend above and below the surface of the upper tray, it is to be understood that this is only an embodiment, and the knife receiving structures can be flush with the top and/or the bottom of the upper tray.

Figure 12:
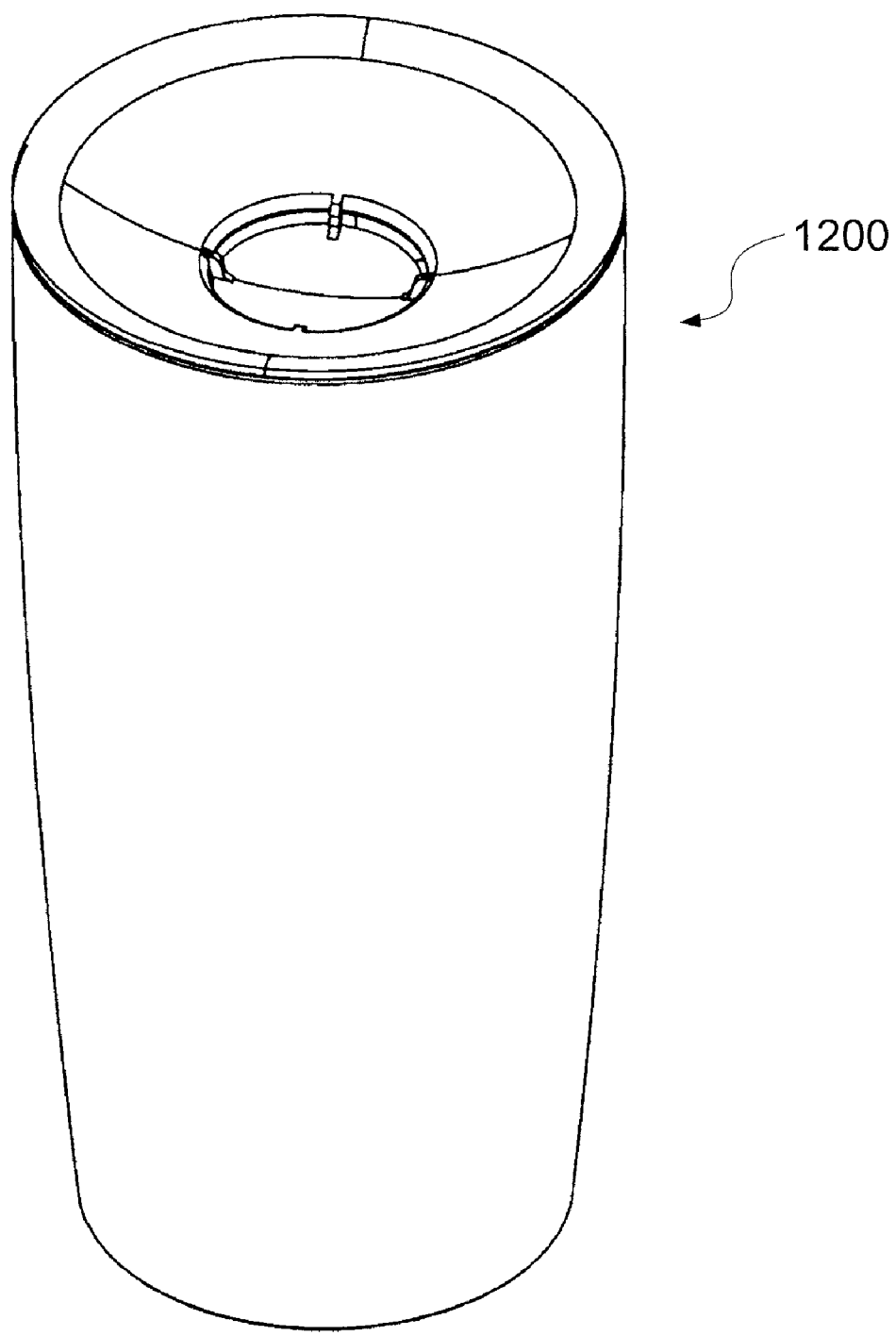
FIG. 12 illustrates an attachment for sanitizing toothbrushes according to an embodiment of the present disclosure, which can be used with the base unit of FIG. 4.

FIG. 12 illustrates an sanitizing container for sanitizing toothbrushes that can be used with the base unit of FIG. 4 according to an embodiment of the present disclosure. The sanitizing container (1200) can include an outer container, a center structure for mating with the outer container, the center structure for receiving toothbrushes to be sanitized, and a lower tray for receiving ends of the toothbrushes to be sanitized.

Figure 13:
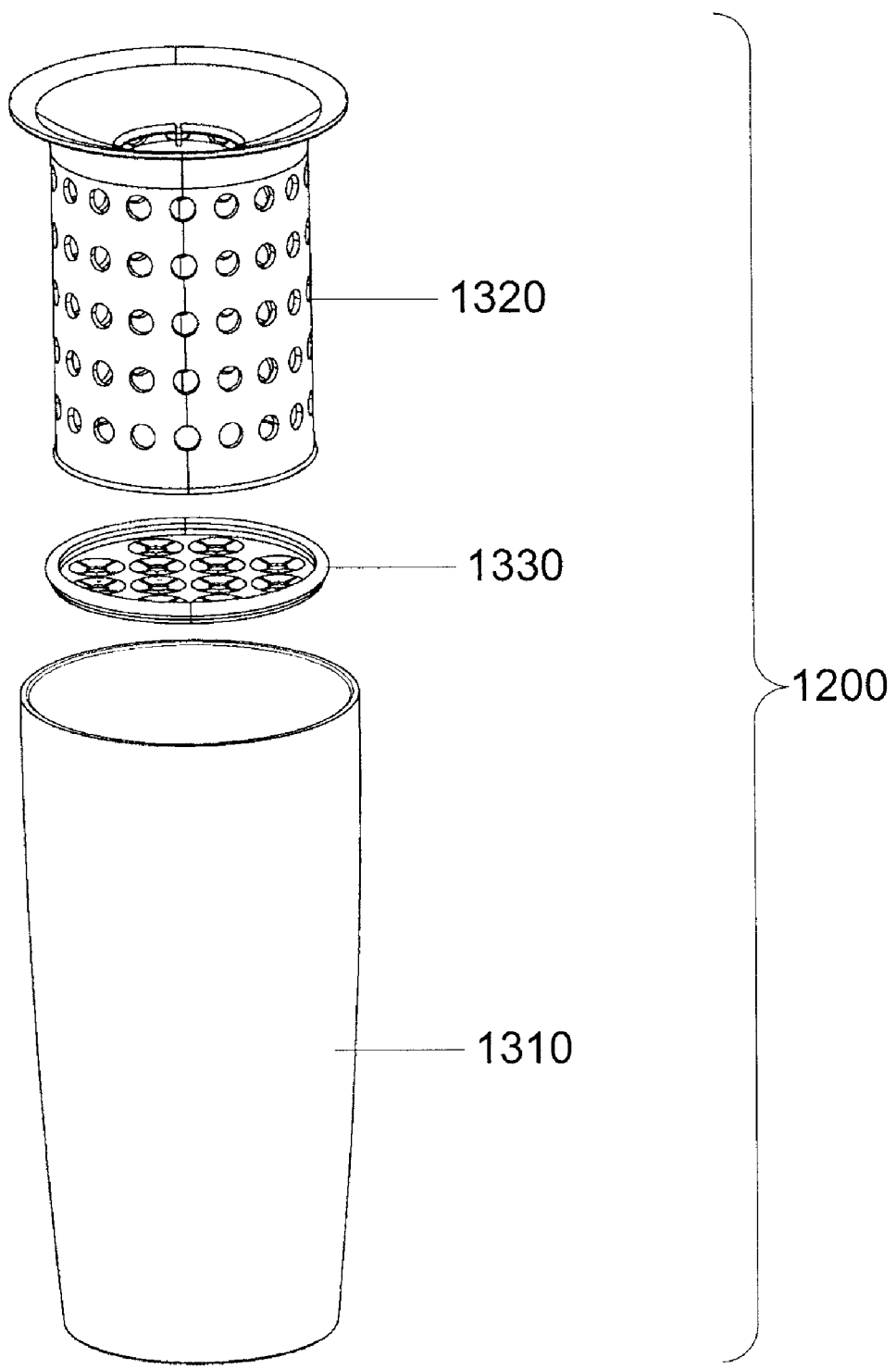
FIG. 13 illustrates an exploded view of the sanitizing container of FIG. 12.

FIG. 13 illustrates an exploded view of the sanitizing container of FIG. 12. The sanitizing container (1200) can comprise an outer container (1310) having an open top and a closed bottom, the outer container preferably being substantially cylindrical, optionally being tapered towards either the bottom or the top. The sanitizing container can also comprise a center structure (1320), for mating with the open top of the outer container. The center structure can have a cylindrical shape, with a sidewall, an open top and a closed base. A particular embodiment of the center structure is shown as having a top portion joined to the top of the sidewall, the top portion including an upper lip for mating with the top of the outer container. The top portion defines at least one opening for ends of the toothbrushes (such as the handle, or the end not having the bristles) from which to protrude. The top portion can preferably include a tapered portion extending from the upper lip, the lower end of the tapered portion defining the opening. A sidewall of the center structure preferably defines a plurality of openings for ozonated water to flow through.

A lower tray (1330) is also shown as being provided for mating with the bottom of the center structure, and for receiving ends of the toothbrushes (such as the working end, or the end having the bristles) to be sanitized. In use, the lower tray can be seated flush with the bottom of the outer container, or can be sized to be seated near the bottom of the outer container. In either case, the bottom tray keeps the toothbrushes from having direct contact with the bottom of the outer container. This is advantageous when a fluid control valve is provided in the base of the outer container, to ensure that the toothbrushes do not interfere with the flow of water into and out of the sanitizing container. It is to be understood that many different embodiments and structures of the sanitizing container are possible, other than the one shown in FIG. 13.

Figure 14:
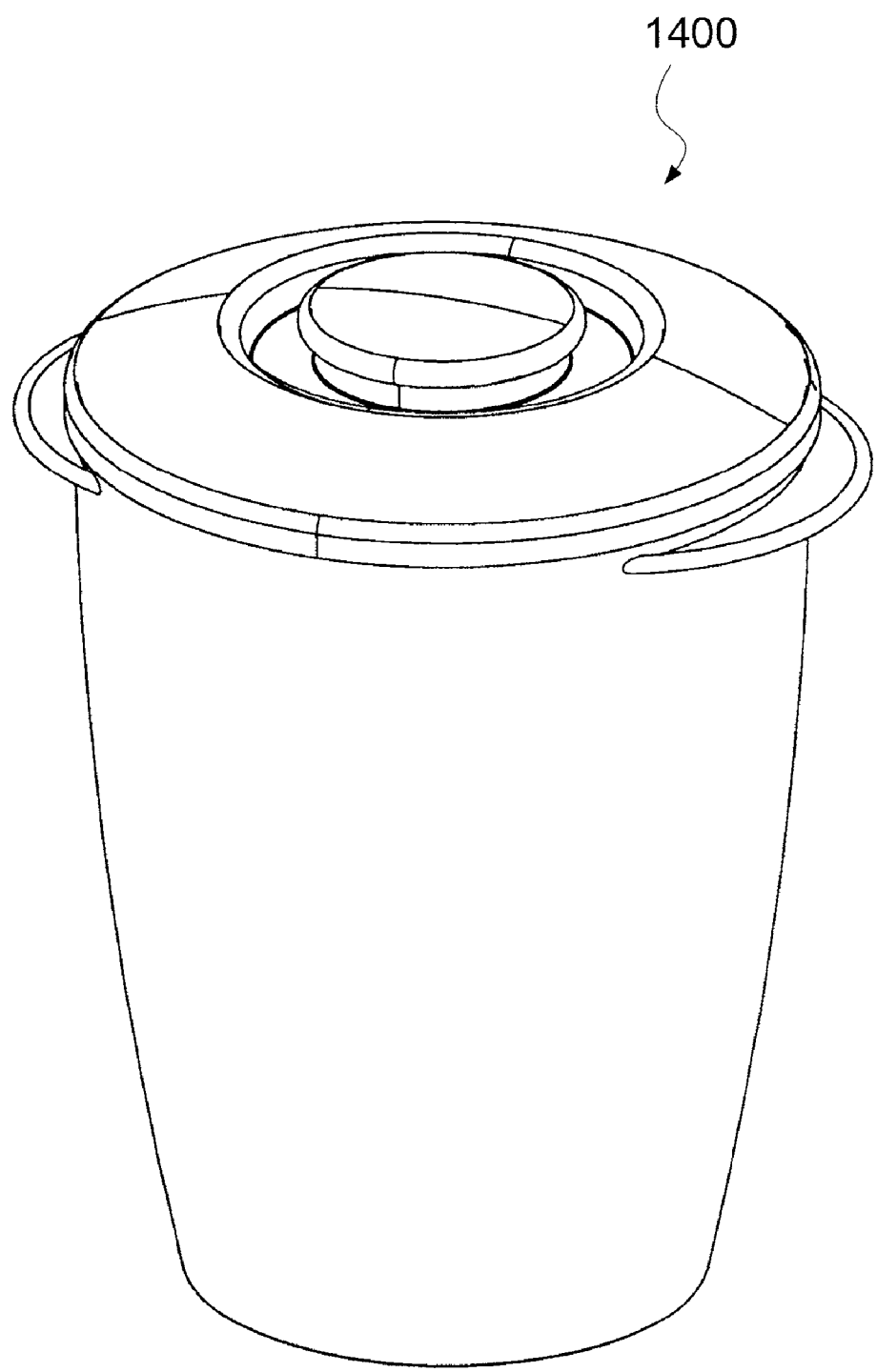
FIG. 14 illustrates an attachment for sanitizing baby bottles according to an embodiment of the present disclosure, which can be used with the base unit of FIG. 4.

FIG. 14 illustrates an sanitizing container for sanitizing baby bottles that can be used with the base unit of FIG. 4 according to an embodiment of the present disclosure. The sanitizing container (1400) can include an outer container, a center portion for mating with the outer container, the center portion for receiving baby bottles to be sanitized, and optionally includes a top cover.

Figure 15:
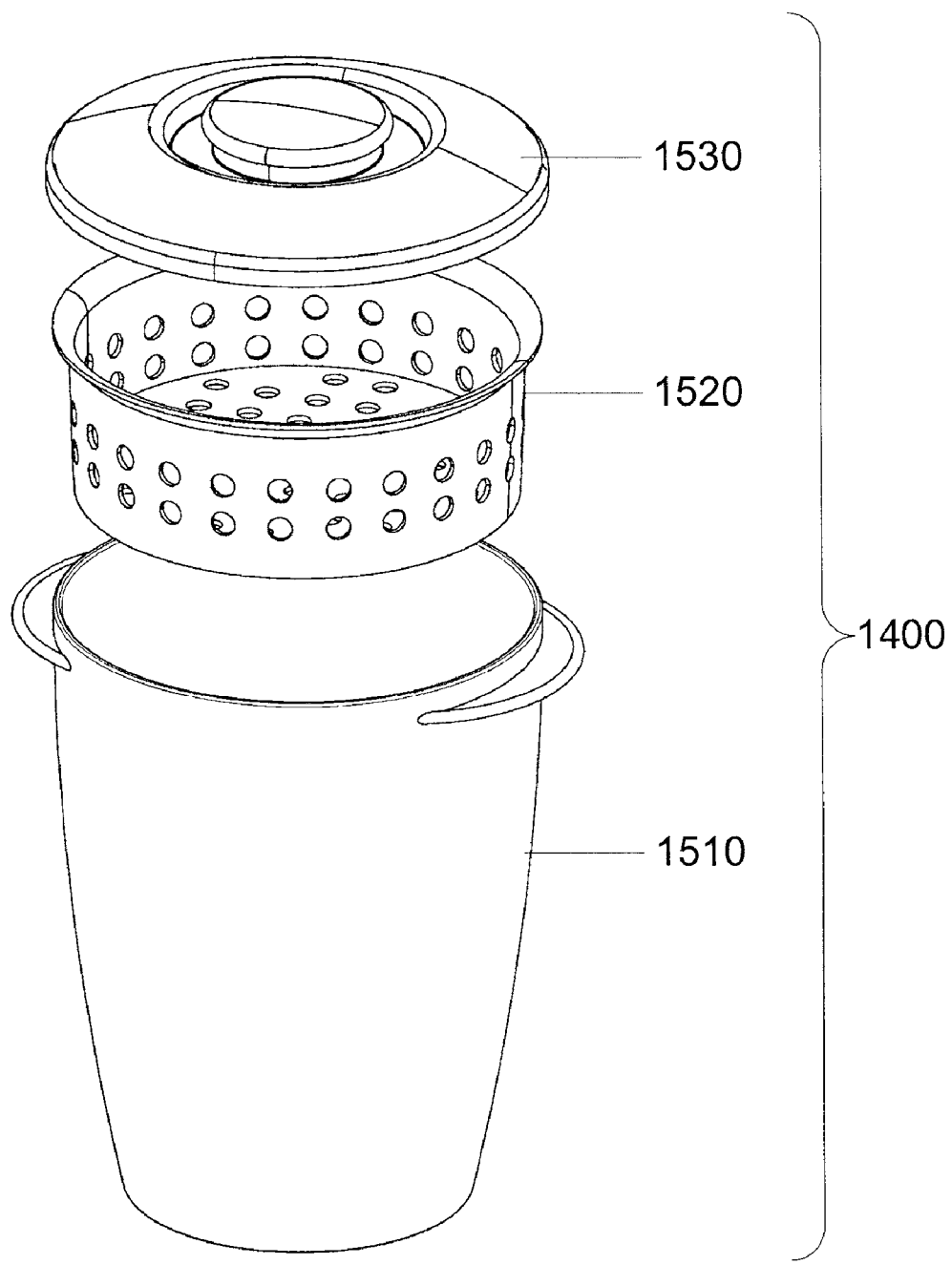
FIG. 15 illustrates an exploded view of the sanitizing container of FIG. 14.

FIG. 15 illustrates an exploded view of the sanitizing container of FIG. 14. The sanitizing container (1400) can comprise an outer container (1510) having an open top and a closed bottom, the outer container preferably being substantially cylindrical, optionally being tapered towards either the bottom or the top. The sanitizing container can also comprise a center structure (1520), for mating with the open top of the outer container. The center structure can have a cylindrical shape, with a sidewall, an open top and a closed base. A particular embodiment of the center structure is shown as having an upper lip joined to the top of the sidewall, the upper lip for mating with the top of the outer container. The top portion defines an opening through which baby bottles can be inserted and removed. The sidewall of the center structure preferably defines a plurality of openings for ozonated water to flow through. The base of the center structure can also define a plurality of openings for ozonated water to flow through. An optional top cover (1530) can be provided, for mating with the upper lip of the sidewall of the center structure. The top cover preferably includes a handle for easy removal and placement of the top cover on the sanitizing container. The top cover helps to maintain a sanitary environment by closing the top to from the surrounding environment.

It is to be understood that many different embodiments and structures of an upper tray are possible, other than the one shown in FIG. 15. For example, the sanitizing container can include a plurality of baby bottle receiving structures. These structures can be integral with the center structure, or can be provided as a separate insert. The baby bottle receiving structures are for receiving baby bottles and keeping them in a position suitable for sanitization and can be cylindrical, conical, or any other suitable shape. The baby bottle receiving structures can also be arranged so as to maximize the use of space in the sanitizing container, and allow a large number of baby bottles to be sanitized at the same time.

Of course, although a particular embodiment has been described with respect to FIGS. 14 and 15 relating to the sanitization of baby bottles, it is obvious to one of ordinary skill in the art that the open space provided in the center structure can be used for the sanitization of any number of different types of items. For example, infant pacifiers and the like could easily be sanitized in the sanitizing container of FIG. 15. In fact, baby bottles or other items could be sanitized in a lower portion of the sanitizing container, while other items are sanitized in the center structure. Moreover, the fact that the base of the center structure is preferably closer to the top of the outer container than at its bottom allows for the easy insertion and removal of the items, without having to dip one's hands in the ozonated water itself. The sanitization base with which these sanitizing containers can be used can be provided in such a way as to ensure that ozonated water will flow into the center structure and sanitize the items contained therein, without requiring the outer container to be completely full of water.

It is also to be understood that many different types of items can be sanitized simultaneously, and each container can be employed for sanitizing any number of different types of items than those with which they have been specifically described herein, either simultaneously or separately. Also, embodiments of the present disclosure can be adapted to provide larger containers and therefore the ability to sanitize larger items and/or greater quantities of items, for example for industrial applications.

Another advantageous application of the sanitizing containers according to embodiments of the present disclosure is the use of an sanitizing container for sanitizing surgical/dental equipment that can be used with the base unit of FIG. 4 according to an embodiment of the present disclosure. It is well known that dentists, doctors, surgeons and other medical professionals require sanitized equipment, and an effective yet simple and relatively inexpensive solution is provided by embodiments of the present disclosure. As has been described above, an sanitizing container can be provided having an outer container, and some sort of inner structure for receiving the medical (surgical, dental, etc.) equipment. The inner structure can be a flat tray such as described in relation to FIG. 15, or it can include a specialized item container such as described in relation to FIGS. 11 and 13. For example, an upper tray can be provided, the upper tray defining a plurality of medical equipment receiving means. The medical equipment receiving means can be shaped and constructed so as to receive various types and sizes of medical equipment, and can extend above and below the surface of the upper tray, or be flush with the top and/or the bottom of the upper tray. Such a system allows for sanitization of medical equipment directly in a dentist's or doctor's office, operating theatre, or any other local environment, without having to send the equipment to an external site to be sanitized. The turn-around time for sanitizing medical equipment can thus be significantly reduced.

Of course, a sanitizing container for sanitizing medical equipment according to an embodiment of the present disclosure can be produced using any type of material, such as a plastic or a metal, in order to satisfy health requirements, but also to satisfy any aesthetic preferences of doctors and dentists, who may prefer sanitizing containers that are not made of plastic, or prefer that they do not look as if they are intended for household use. For example, an inner portion of such a sanitizing container can be made of plastic, while an outer portion of the sanitizing container can be made of a more aesthetically pleasing material, such as titanium, high quality wood, and the like. It is to be understood that any number of suitable materials can be used for construction of the sanitizing container and its constituent parts. Similar materials could be used for the casing of the base. The purification technology, controls and other components typically housed within the base could alternatively be built in to a sanitizing station on a countertop in a medical facility or office, or any other alternative installation where the components are used in perhaps a different physical implementation.

Although embodiments of the present disclosure describe the use of these sanitizing containers with a base system that sanitizes using ozonated water, it is to be understood that the sanitizing containers are independent of the type of sanitization used. As such, these sanitizing containers can be used with any type of sanitization or purification system as described herein or as known to those of ordinary skill in the art, and any physical modifications that would be necessary would be obvious to one of ordinary skill in the art.

The above-described embodiments of the present disclosure are intended to be examples only. Alterations, modifications and variations may be effected to the particular embodiments by those of skill in the art without departing from the scope of the disclosure, which is defined solely by the claims appended hereto.

What is claimed is:

1. A water purification system comprising:
 a water container including
 an upper reservoir for receiving unfiltered water, said upper reservoir having a lower opening;
 a filtering medium within the lower opening of the upper reservoir for filtering unfiltered water passing therethrough;
 a lower reservoir for receiving water passed through the filtering medium, said lower reservoir having a lower opening;
 wherein said filtering medium is located above and not extending into the lower reservoir; and
 a base for receiving the water container in fluid communication with the lower opening of the lower reservoir, said base comprising a purification technology for purification of water received from the lower reservoir; and a water circulator for circulating water between the lower reservoir and the purification technology.

2. The water purification system according to claim 1, wherein said water circulator comprises a pump, connections, and electronic controls.

3. The water purification system according to claim 1 wherein the base additionally comprises an ozone contacting device.

4. The water purification system according to claim 1 wherein the purification technology is selected from the group consisting of:
 a pair of electrodes for generating an electric field;
 a membrane of ultra, micro or nanofiltration;
 an ozone generator in combination with an ozone destructor and a centrifugal degasser;
 an ultraviolet (UV) light source; and
 an aeration or oxygenation device.

5. The water purification system according to claim 4, wherein the purification technology comprises an aeration or oxygenation device, and wherein atmospheric oxygen or pure oxygen is injected into the water via a venturi system.

6. The water purification system according to claim 5, wherein the water container additionally comprises a sparger positioned in the lower reservoir above the lower opening.

7. The water purification system according to claim 1 wherein said filtering medium is selected from the group consisting of:
   a granulated activated carbon (GAC) cartridge; an extruded carbon sheet between layers of fabric material; an ion exchange resin; and one or more layers of fabric material.

8. The water purification system of claim 1, additionally comprising a fluid transfer port which interfaces with the base and the drinking water filtration device.

9. The water purification system of claim 8, wherein said double check valve comprises:
   a) an outer body having an inlet and an outlet, with the first and second valve stems contained on said outer body;
   b) the outlet in the outer body being the valve seat to said second valve stem; the first valve stem being smaller than the second valve stem, and contained within the second, wherein said valve stems operate along a common axis; the second valve stem having a cylindrical conduit passing therethrough in which the first valve stem is contained, and having a valve seat for the first valve stem therein; and
   c) springs surrounding said first and second valve stems and acting on said valves to engage respective valve seats.

10. The water purification system of claim 2, wherein said electronic controls comprise an auto-sensing circuit which detects the presence of the filtration device on the base, activates an appropriate program, and illuminates a ready light.

11. The water purification system of claim 10, wherein said program is initiated when a user pushes a start button when said ready light is illuminated.

12. The water purification system of claim 11, wherein said program comprises a treatment period controlled by time and/or concentration, said treatment period consisting of:
   a) drawing water from the lower reservoir via a pump,
   b) pumping water from (a) through the purification technology,
   c) directing water from (b) back into the lower reservoir; and
   d) communicating to the user via a light and/or audible alarm indicating that the container can be removed from the base.

* * * * *